US006156512A

United States Patent [19]
Schumm et al.

[11] Patent Number: 6,156,512
[45] Date of Patent: *Dec. 5, 2000

[54] ALLELIC LADDERS FOR SHORT TANDEM REPEAT LOCI

[76] Inventors: James W. Schumm, 5843 Timber Ridge Trail, Madison, Wis. 53711; Katherine A. Micka, 1842 Paddock Pl., Oregon, Wis. 53575; Dawn R. Rabbach, 6649 Wendell Way, DeForest, Wis. 53532

[*] Notice: This patent is subject to a terminal disclaimer.

[21] Appl. No.: 09/031,353

[22] Filed: Feb. 26, 1998

Related U.S. Application Data

[63] Continuation-in-part of application No. 08/652,143, May 23, 1996, abandoned.

[51] Int. Cl.[7] .............................. C12Q 1/68; C12P 19/34; C07H 21/04
[52] U.S. Cl. ........................... 435/6; 435/91.2; 536/23.1; 536/24.3; 536/24.31; 536/24.33
[58] Field of Search ................................. 536/23.1, 24.3, 536/24.31, 24.33; 435/6, 91.2

[56] References Cited

U.S. PATENT DOCUMENTS

| | | | |
|---|---|---|---|
| 4,855,225 | 8/1989 | Fung et al. | |
| 5,192,659 | 3/1993 | Simons | |
| 5,364,759 | 11/1994 | Caskey et al. | 435/6 |
| 5,599,666 | 2/1997 | Schumm et al. | 435/6 |
| 5,674,686 | 10/1997 | Schumm et al. | 435/6 |
| 5,783,406 | 7/1998 | Schumm et al. | 435/6 |
| 5,843,660 | 12/1998 | Schumm et al. | 435/6 |

OTHER PUBLICATIONS

Alford, RL, et al., *Am J. Human Genet*. 55: 190–195 (1994).
Hammond, HA, et al., *Am J. Human Genet*. 55: 175–189 (1994).
Kimpton et al. *Human Molecular Genetics* vol. 1(4): 287, Jul. 1992.
Puers, C., et al., "Analysis of Polymorphic Short Tandem Repeat Loci Using Well–Characterized Allelic Ladders" *Fourth International Symposium on Human Identification 1993*, pp. 161–172.
Schumm et al. "Development of Nonisotopic Multiplex Amplification Sets for Analysis of Polymorphic STR Loci" *Fourth International Symposium on Human Identification 1993*, pp. 177–187.
Utah Marker Development Group, *Am J Hum Genet*. 57: 619–628 (1995).
Wall et al., *Human Molecular Genetics* vol. 2(7): 1023–1029 Jul. 1993.
Bassam et al. (1991) *Anal. Biochem*.196:80–83.
Beckmann and Weber (1992) *Genomics* 12:627–631.
Botstein et al. (1980) *Am. J. Hum. Genet*. 32:314–331.
Boulikas and Hancock (1981) *J. Biochem. Biophy. Meth*. 5:219–228.
Brinkmann (1992) *Proceedings from the Third International Symposium on Human Identification* (Promega, Madison, WI) pp. 357–373.
Brunk et al. (1979) *Anal Biochem* 92:497–500.
Budowle et al. (1991) *Am J Hum Genet* 48:137–144.
Edwards et al. (1991a) *Proceedings from the Second International Symposium on Human Identification* (Promega Corporation) p. 31–52.

(List continued on next page.)

*Primary Examiner*—Kenneth R. Horlick
*Attorney, Agent, or Firm*—Michael Best & Friedrich LLP; Grady J. Frenchick; Karen B. King

[57] ABSTRACT

Allelic ladders of short tandem repeat (STR) loci selected from the group consisting of D16S539, D7S820, D13S317, and D5S818; methods for their use in analyzing STR polymorphisms, and kits containing the allelic ladders are disclosed.

20 Claims, 9 Drawing Sheets

Application of Allelic Ladders
for Typing of Individuals

OTHER PUBLICATIONS

Edwards et al. (1991b) *Am J Hum Genet* 49:746–756.
Edwards (1992) *Genomics* 12:241–253.
Frank and Koster (1979) *Nucleic Acids Res.* 6:2069–2087.
Gill et al. (1985) *Nature* 318:577–579.
Grimberg et al. (1989) *Nucl. Acids Res.* 17:8390.
Higuchi (1989) *Amplifications: A Forum for PCR Users* (May 1989), Perkin Elmer Cetus, Norwalk, CT, Issue 2.
Jeffreys et al. (1985) *Nature* 316:76–79.
Jones (1972) *J. Forensic Sci. Soc.* 12:355–359.
Kan et al. (1974) *Nature*, 251:392.
Kan et al. (1977) *N. Engl. J. Med.,* 297:1080–1084.
Kan et al. (1978) *PNAS*, 75:5631–5635.
Litt and Luty (1989) *Am J Hum Genet* 44:397–401.
Martin et al. (1991) *BioTechniques* 11:110–113.
Maxam and Gilbert (1977) *Proc. Natl. Acad. Sci. USA* 74:560.
Maxam and Gilbert (1980) *Meth. Enzymol.* 65:499.
Miller et al. (1988) *Nucl. Acids Res.* 16:1215.
Nakamura et al. (1987) *Science* 235:1616–1622.
Patel et al. (1984) *Somat Cell Mol Genet* 10:483–493.
Puers et al. (1993) *Am. J. Hum. Genet.,* 53:953–958.
Sambrook et al. (eds) (1989) *Molecular Cloning—A Laboratory Manual,* 2nd edition, Cold Spring Harbor Laboratory Press.
Sanger et al. (1977) *Proc. Natl. Acad. Sci. USA* 74:5463–5467.
Smith (1995) Biotechniques 18:122–128.
Somerville and Wang (1981) *Biochem. Biophys. Res. Comm.* 102: 53–58.
Sprecher et al. (1996) *BioTechniques* 20:266–276.
Tautz (1989) *Nucleic Acids Res.* 17:6463–6471.
Voss et al (1992) *Meth. Mol. Cell Biol.,* 3:30–34.
Walsh et al. (1991) *BioTechniques* 10:506–513.
Watson, J.D. et al. (1987) *Mol. Biol. Gene,* The Benjamin/Cummings Publishing Company, Inc., California, pp. 274–276.
Weber and May (1989) *Am J Hum Genet* 44:388–396.

D16S539

Allelic Ladder

Alleles

D16S539

Allelic Ladder

Alleles

D7S820

Allelic Ladder

Alleles

D7S820

Allelic Ladder

Alleles

D13S317

Allelic Ladder

Alleles

D13S317

Allelic Ladder

D5S818

Allelic Ladder

Alleles

Application of Allelic Ladders for Typing of Individuals

ALLELIC LADDERS FOR SHORT TANDEM REPEAT LOCI

This is a Continuation-in-Part of application Ser. No. 08/652,143, filed May 23, 1996 abandoned.

FIELD OF THE INVENTION

The present invention is generally directed to the use of genetic analysis for the detection of short tandem repeat sequence polymorphisms in individuals. Specifically, the invention is directed to allelic ladders which function as marker standards for detecting short tandem repeat (STR) polymorphisms.

BIBLIOGRAPHY

Full bibliographic citations for the references cited hereinbelow can be found in the Bibliography, immediately preceding the claims.

DESCRIPTION OF THE PRIOR ART

Classical approaches to size determination compare unknown DNA fragments to DNA fragments of completely different sequences but of known molecular weight. Size standards are generally prepared by restriction digestion of plasmid or lambda phage DNA or by polymerase chain reaction (PCR) amplification of well-characterized templates. This method, however, suffers from the phenomenon that different DNA sequences may produce distinct DNA conformation dynamics resulting in different mobilities of fragments of identical molecular weight, Frank and Koster (1979). Thus, standards and sample DNA fragments of identical molecular weight may appear as distinct bands in gel electrophoresis.

Many loci in at least the human genome contain a polymorphic short tandem repeat (STR) region. STR loci consist of short, repetitive sequence elements of 3 to 7 base pairs in length. It is estimated there are 200,000 expected trimeric and tetrameric STRs present as frequently as once every 15 kb in the human genome, Edwards et al. (1991b) and Beckmann and Weber (1992). Nearly half of the STR loci studied by Edwards et al. (1991b) are polymorphic, providing a rich source of genetic markers. Variation in the number of repeat units at a particular locus is responsible for the observed polymorphism reminiscent of VNTR loci, (Nakamura et al. (1987), and minisatellite loci Jeffreys et al. (1985), which contain longer repeat units, and microsatellite of dinucleotide repeat loci. See, for instance, Litt and Luty (1989), Tautz (1989), Weber and May (1989), and Beckmann and Weber (1992).

Polymorphic STR loci are extremely useful markers for human identification, paternity testing and genetic mapping. Polymorphic STR's are characterized by a single, predominant repeating motif, with the polymorphism arising in the number of integral times in which the motif is repeated. Polymorphic STR loci are amplified via PCR by employing specific primer sequences identified in the regions flanking the tandem repeat.

Allelic forms of these loci are differentiated by the number of copies of the repeat sequence contained within the amplified region and are distinguished from one another following electrophoretic separation by any suitable detection method including radioactivity, fluorescence, silver stain, ethidium bromide and color.

Alleles are named according to the number of repeat units which are contained within them, Edwards et al. (1991). For example, an allele containing eight contiguous identical copies of the repeat is called "allele 8" while one containing ten such copies is called "allele 10."

The first publication describing an allelic ladder is Budowle et al. (1991). This work describes mixing of amplified alleles of the D1S80 locus from several individuals to create a size marker simplifying additional analysis of samples amplified at this locus. In this case, amplified alleles were detected following electrophoretic separation using a silver stain method.

Allelic ladders for several STR loci have been described. See, for instance Edwards et al. (1991b), Puers et al. (1993), Smith (1995), and Sprecher et al. (1996). A strategy similar to Budowle et al's. was employed to generate the allelic ladders. Several amplified alleles for the STR loci were derived from independent genomic DNA samples, mixed, and subjected to electrophoretic separation. The separated alleles were labeled by inclusion of a fluorescently labeled primer in each amplification reaction. The amplification products were visualized using a fluorescence detector.

SUMMARY OF THE INVENTION

The invention is directed to an allelic ladder of a short tandem repeat locus. The allelic ladder comprises, in combination, an isolated plurality of DNA molecules which are allelic variants of a polymorphic short tandem repeat locus. Each DNA molecule of the plurality comprised a polymorphic tandemly repeated base pair motif and non-polymorphic 5' and 3' flanking regions. The DNA molecules are derived from polymorphic short tandem repeat loci selected from the group consisting of D16S539, D7S820, D13S317, and D5S818.

The invention is further drawn to a kit for analyzing short tandem repeat sequences from a DNA sample. The kit comprises at least one receptacle containing one or more allelic ladders as described in the immediately preceding paragraph.

The invention is still further drawn to a kit for analyzing short tandem repeat sequences from a DNA sample which comprises at least one receptacle containing a combined plurality of DNA molecules. Each DNA molecule has at least one tandemly repeated nucleotide base sequence motif, and wherein in the combined plurality of DNA molecules the at least one motif is repeated within a corresponding numeric integer repeat range. The motif and its corresponding numeric integer repeat range are selected from the group consisting of:

GATA within a repeat range of from 5 to 14, and
AGAT within a repeat range of from 7–14.

The invention is also drawn to a method for detecting and identifying alleles of a short tandem repeat sequence from DNA. The method comprises amplifying at least one short tandem repeat sequence from a target DNA by polymerase chain reaction using locus-specific oligonucleotide primers, wherein the at least one short tandem repeat sequence is located within at least one short tandem repeat locus selected from the group consisting of D16S539, D7S820, D13S317, D5S818, and combinations thereof; and then comparing the at least one amplified short tandem repeat sequence to an allelic ladder as described herein. The invention also includes a method for simultaneously detecting and identifying alleles of four short tandem repeat sequences from DNA which comprises co-amplifying four short tandem repeat sequences from a target DNA by polymerase chain reaction using locus-specific oligonucleotide primers for the four short tandem repeat sequences, wherein the four short tandem repeat sequences are located within four short tandem repeat loci selected from the group consisting of D16S539, D7S820, D13S317, D5S818; and then comparing the four co-amplified short tandem repeat sequences to allelic ladders corresponding to each of the four short tandem repeat loci.

The allelic ladders of the present invention have been characterized by sequence analysis, thereby allowing confident, rapid, and precise assignment of discretely defined alleles. The DNA fragments included within the allelic ladders are identical in size and sequence to amplified alleles from sample material from which they were derived. Each allelic ladder is a combined plurality of amplified DNA molecules which are allelic variants of STR loci which include the polymorphic repeated region and the non-polymorphic flanking regions. Thus, co-migration of allelic ladder fragments and sample fragments is achieved regardless of the gel system used for electrophoretic separation. Use of the allelic ladders in combination with specific electrophoretic and detection techniques described herein allows discrimination of variants differing by as little as a single base pair.

The assignment of alleles using a well-defined allelic ladder is precise, reliable, simple, and easily automated. The method can be practiced using several different separation and detection means. Additionally, the ladders can be used simultaneously in multiplex PCR amplifications. This speeds the time needed to perform an analysis at several different loci considerably.

The application of allelic ladders accelerates, simplifies, and allows precise characterization of unknown alleles.

These locus-specific standard size markers are also useful tools for the identification of microheterogeneity, i.e., length variations not resulting from integral variation in the number of tandem repeats, at STR loci.

The construction, characterization, and application of allelic ladders permits rapid, reliable characterization of unknown alleles without requirement for calculations or analytical equipment. In essence, the allelic ladder acts as a locus-specific high resolution size marker.

Uses for this process include forensic analysis, paternity determination, monitoring of bone marrow transplantation, linkage mapping, and detection of genetic diseases, including cancers.

The allelic ladders can be used to determine allele frequencies, frequencies of heterozygosity, polymorphism information content (PIC), Botstein et al. (1980), and matching probability (pM), Jones (1972).

These and other aims, objects, and advantages of the present invention will become evident upon a complete reading of the Detailed Description, claims, and attached drawing figures, below.

DETAILED DESCRIPTION OF THE INVENTION

Figure 1A:
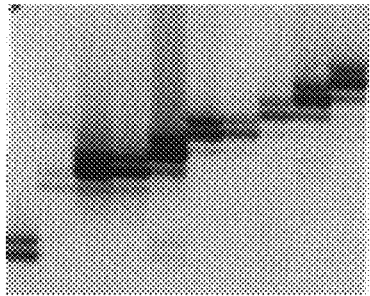
FIG. 1A is a photograph illustrating a silver stain detection of the individual alleles used in the construction of the D16S539 allelic ladder described in Example 1. The lanes labeled 5, 8, 9, 10, 11, 12, 13, and 14 indicate the repeat number of each allele.

The following definitions are included to provide a clear and consistent understanding of the terms used herein:

Allelic ladder: a standard size marker comprising an isolated plurality of DNA molecules which are allelic variants of a polymorphic short tandem repeat locus, each DNA molecule comprising a polymorphic tandemly repeated base pair motif and non-polymorphic 5' and 3' flanking regions.

Allele: a genetic variation associated with a segment of DNA, i.e., one of two or more alternate forms of a DNA sequence occupying the same locus.

Biochemical nomenclature: standard biochemical nomenclature is used herein in which the nucleotide bases are designated as adenine (A), thymine (T), guanine (G), and cytosine (C). Corresponding nucleotides are, for example, deoxyguanosine-5'-triphosphate (dGTP).

DNA polymorphism: the condition in which two or more different nucleotide sequences coexist in the same interbreeding population in a DNA sequence.

Locus (or genetic locus): a specific position on a chromosome. Alleles of a locus are located at identical sites on homologous chromosomes.

Locus-specific primer: a primer that specifically hybridizes with a portion of the stated locus or its complementary strand, at least for one allele of the locus, and does not hybridize efficiently with other DNA sequences under the conditions used in the amplification method.

Polymerase Chain Reaction (PCR): a technique in which cycles of denaturation, annealing with primer, and extension with DNA polymerase, are used to amplify the number of copies of a target DNA sequence by $>10^6$ times. The polymerase chain reaction process for amplifying nucleic acid is covered by U.S. Pat. Nos. 4,683,195 and 4,683,202, which are incorporated herein by reference for a description of the process.

Polymorphism information content (PIC): Because matings between two individuals who are both heterozygous but have identical genotypes are often not useful in genetic analysis, PIC was defined to more accurately reflect true informativeness, Botstein et al. (1980). PIC values range from 0 to 1.0, and are smaller in value than heterozygosities. For markers that are highly informative (heterozygosities exceeding about 70%), the difference between heterozygosity and PIC is slight.

Primary reaction: initial reaction using purified human genomic DNA as a template for the PCR.

Primers: single-stranded oligonucleotides or DNA fragments which hybridize to DNA sequences flanking a locus and prime the PCR.

Primer pair: a matched set of primers including a 5' upstream primer that hybridizes with the 5' end of the DNA sequence to be amplified and a 3' downstream primer that hybridizes with the complement of the 3' end of the sequence to be amplified.

Primer site: the area of the target DNA to which a primer hybridizes.

Secondary reaction: reamplification with the same or different primer pair using a dilution of the primary reaction as template for the PCR.

General Procedure for Constructing Allelic Ladders

The system of the present invention provides a rapid, non-isotopic method which can be used to evaluate very small amounts (e.g., 1 ng) of human DNA. The preferred process includes the use of silver staining to detect the presence of amplified STR products following their separation by denaturing polyacrylamide gel electrophoresis (PAGE). It is also possible to detect STR products using radioactivity, fluorescence, and various dyes or stains with denaturing or native gel electrophoresis using any available gel matrix or size separation method.

Allelic ladders are constructed for STR loci with the goal of including several or all known alleles with lengths corresponding to amplified fragments containing an integral number of copies of polymorphic sequences. While it is preferred to have integral number of copies for commercial applications, the integral number of copies of repeats is not essential to the concept of allelic ladders.

DNA samples used to identify allelic ladder components of a specific locus are obtained and subjected to DNA isolation, PCR amplification, electrophoretic separation, and determination of the length heterogeneity. DNA sequence analysis of amplified fragments is often used to confirm the nature of the observed length heterogeneity. The basic process for constructing allelic ladder utilizes the following techniques:

Obtaining DNA Samples

Several individuals are selected for DNA isolation. It is preferable to select individuals from a variety of ethnic groups to increase the probability of identifying a greater number of alleles. DNA is isolated from blood or tissue culture cells using standard methods. See, for instance, Patel et al. (1984) and Gill et al. (1985). DNA concentrations are easily measured fluorometrically, Brunk et al. (1979).

Amplification

Human genomic DNA samples are subjected to PCR amplification using primers and thermocycling conditions specific for each locus. Reference is made to the following Table 1 for the primer sequences used in development of the allelic ladders of the present invention.

TABLE 1

| Locus | Primer Sequences | SEQ. ID. NO: |
|---|---|---|
| D16S539 | primer 1: GGG GGT CTA AGA GCT TGT AAA AAG | 1 |
| | primer 2: TGT GCA TCT GTA AGC ATG TAT CTA TC | 2 |
| D7S820 | primer 1: GAA CAC TTG TCA TAG TTT AGA ACG | 3 |
| | primer 2: CTG AGG TAT CAA AAA CTC AGA GG | 4 |
| D13S317 | primer 1: ACA GAA GTC TGG GAT GTG GA | 5 |
| | primer 2: GCC CAA AAA GAC AGA CAG AA | 6 |
| D5S818 | primer 1: GGG TGA TTT TCC TCT TTG GT | 7 |
| | primer 2: TGA TTC CAA TCA TAG CCA CA | 8 |
| D7S820 | primer 1: ATG TTG GTC AGG CTG ACT ATG | 9 |
| | primer 2: CCA CAT TTA TCC TCA TTG ACA G | 10 |
| D7S820 | primer 1: ATG TTG GTC AGG CTG ACT ATG | 9 |
| | primer 2: TCC ACA TTT ATC CTC ATT GAC AG | 11 |
| D5S818 | primer 1: GGG TGA TTT TCC TCT TTG GTA TCC | 12 |
| | primer 2: AGT GAT TCC AAT CAT AGC CAC AG | 13 |

Reference is made to the Examples below for details on the specific amplification procedure and primer sequences relating to each locus and each allelic ladder. The locus-specific primers hybridize solely with alleles of the loci to be amplified. Reference is made to U.S. Pat. No. 5,192,659, to Simons, which is incorporated herein by reference for its description of locus-specific primers.

For some loci the primary or secondary reactions were mixed together and then amplified again. For others the individual alleles were purified from polyacrylamide gels prior to being mixed.

The nucleotide base sequences of several different alleles of the D16S539, D7S820, D13S317, and D5S818 loci, including the polymorphic repeat regions and the non-polymorphic 5' and 3' flanking regions, have been described and are available from the Cooperative Human Linkage Center. Illustrative alleles from these loci appear as follows. The forward primers of the above-noted primer pairs for these loci are underlined; the complement of the reverse primers are boxed.

D16S539

| ATGGCTGCCC | TCACGGCTGC | ACCGGGAGGA | TGACTGTNTT | CCCACTCTCA |
| GTCCTGCCGA | GGTGCCTGAC | AGCCCTGCAC | CCAGGAGCTG | GGGGGTCTAA |
| GAGCTTGTAA | AAAGTGTACA | AGTGCCAGAT | GCTCGTTGTG | CACAAATCTA |
| AATGCAGAAA | AGCACTGAAA | GAAGAATCCA | GAAAACCACA | GTTCCCATTT |
| TTATATGGGA | GCAAACAAAG | GCAGATCCCA | AGCTCTTCCT | CTTCCCTAGA |
| TCAATACAGA | CAGACAGACA | GGTGGATAGA | TAGATAGATA | GATAGATAGA |
| TAGATAGATA | GATAGATATC | ATTGAAAGAC | AAAACAGAGA | TGGATGATAG |
| ATACATGCTT | ACAGATGCAC | ACACAAACGT | AAATGGTATN | AAAAATNGGA |
| TNCACTCTTG | TANGGTTGTT | NTTACC | | |

SEQ. ID. NO: 14. (SEQ. ID. NO: 1 is underlined; the complement of SEQ. ID. NO: 2 is boxed.) The repeat motif in the D16S539 locus is GATA. The Cooperative Human Linkage Center database lists 10 known alleles. SEQ. ID. NO: 14 depicts allele 11 of D16S539 (that is, 11 repeats). See SEQ. ID. NO: 14, nt's 275 to 318.

D7S820

| AATTTTTGTA | TTTTTTTTAG | AGACGGGGTT | TCACCATGTT | GGTCAGGCTG |
| ACTATGGAGT | TATTTTAAGG | TTAATATATA | TAAAGGGTAT | GATAGAACAC |
| TTGTCATAGT | TTAGAACGAA | CTAACGATAG | ATAGATAGAT | AGATAGATAG |
| ATAGATAGAT | AGATAGATAG | ATAGACAGAT | TGATAGTTTT | TTTTTATCTC |
| ACTAAATAGT | CTATAGTAAA | CATTTAATTA | CCAATATTTG | GTGCAATTCT |
| GTCAATGAGG | ATAAATGTGG | AATCGTTATA | ATTCTTAAGA | ATATATATTC |
| CCTCTGAGTT | TTTGATACCT | CAGATTTTAA | GGCC | |

SEQ. ID. NO: 15. (SEQ. ID. NO: 3 is underlined; the complement of SEQ. ID. NO: 4 is boxed.) The repeat motif in the D7S820 locus is GATA. The Cooperative Human Linkage Center database lists 8 known alleles. SEQ. ID. NO: 15 depicts allele 12 of D16S539. See SEQ. ID. NO: 15, nt's 126 to 173.

D13S317

| TGGGATGGGT | TGCTGGACAT | GGTATCACAG | AAGTCTGGGA | TGTGGAGGAG |
| AGTTCATTTC | TTTAGTGGGC | ATCCGTGACT | CTCTGGACTC | TGACCCATCT |
| AACGCCTATC | TGTATTTACA | AATACATTAT | CTATCTATCT | ATCTATCTAT |
| CTATCTATCT | ATCTATCTAT | CTATCTATCA | ATCATCTATC | TATCTTCTG |
| TCTGTCTTTT | TGGGCTGCCT | ATGGCTCAAC | CCAAGTTGAA | GGAGGAGATT |
| TGACCAACAA | TTCAAGCTCT | CTGAATATGT | TTTGAA | |

SEQ. ID. NO: 16. (SEQ. ID. NO: 5 is underlined; the complement of SEQ. ID. NO: 6 is boxed.) The repeat motif in the D13S317 locus is TATC. The Cooperative Human Linkage Center database lists 7 known alleles. SEQ. ID. NO: 16 depicts allele 13 of D16S539. See SEQ. ID. NO: 16, nt's 128 to 179.

D5S818

| | | | | |
|---|---|---|---|---|
| TCTAATTAAA | GTGGTGTCCC | AGATAATCTG | TACTAATAAA | AGTATATTTT |
| AATAGCAAGT | ATGTGACAAG | GGTGATTTTC | CTCTTTGGTA | TCCTTATGTA |
| ATATTTTGAA | GATAGATAGA | TAGATAGATA | GATAGATAGA | TAGATAGATA |
| GATAGGTAGA | TAGAGGTATA | AATAAGGATA | CAGATATAGN | TACAAATGTT |
| GTAAAC TGTG | GCTATGATTG | GAATCA CTTG | GCTAAAAAGC | GCTNAAGCNT |
| TCCTCTGNGA | GAGGCAATTA | CTTTTTTNCT | TAGGNACTNC | CTCANCAGTC |
| TNTTNGC | | | | |

SEQ. ID. NO: 17. (SEQ. ID. NO: 7 is underlined; the complement of SEQ. ID. NO: 8 is boxed.) The repeat motif in the D5S818 locus is AGAT. The Cooperative Human Linkage Center database lists 7 known alleles. SEQ. ID. NO: 17 depicts allele 11 of D5S818. See SEQ. ID. NO: 17, nt's 110 to 153.

Separation and Detection of DNA Fragments

Amplification products are then separated by electrophoresis, for example by denaturing polyacrylamide gel electrophoresis (PAGE), Sambrook et al. (1989). The DNA is then visualized by any number of techniques, including silver staining, radioactive labelling, or fluorescent labelling. See, for instance, Bassam et al. (1991). A permanent record of the data can be generated with the use of automatic processor compatible (APC) film (STR systems manual #TMD004, Promega Corporation, Madison, Wis.).

Analysis of STR Fragments

Following electrophoretic separation and visualization of amplified alleles, individual DNA samples containing potential ladder alleles are identified. Samples are selected based upon the expected band separation for molecular weight differences corresponding to integral numbers of repeat units.

In many cases, the selected amplified alleles are subjected to sequence analysis to confirm the sequence heterogeneity among various alleles. The DNA sequencing technique of Sanger et al. (1977), an enzymatic dideoxy chain termination method was employed. Reference is made to Chapter 13 of Sambrook, J. et al. (1989), which is incorporated herein by reference, for a description of DNA sequencing in general and various DNA sequencing techniques.

Isolation of Amplified Alleles from Heterozygous Individuals

In some cases, isolation of an amplified allele is required prior to mixing the ladder components. Following separation by gel electrophoresis, amplified alleles from either primary or secondary reactions are subjected, for example, to denaturing PAGE. The bands are visualized according to methods known in the art. For example, one known method is by using 0.5 µg/ml ethidium bromide and a transilluminator.

Amplified allelic ladder components, separated using PAGE, are purified by excising the amplified fragment from the gel. The individual gel fragments are soaked 4 hours to overnight at 37° C. in 100–400 µl of TE (10 mM tris pH 7.5, 1 mM EDTA). The gel slice/TE slurry is placed in an "ULTRAFREE"®-MC 0.45 µm filter unit (Millipore, Bedford, Mass.) and spun for approximately 2 minutes in a microfuge to remove acrylamide from the mixture. The isolated fragments may, if necessary, then be diluted, reamplified, and purified using methods known to the art. One method for purifying is by the Magic™PCR kit DNA purification system (Promega, Cat. No. A7170).

Purity of individual alleles is determined by a PCR reaction using a dilution of the gel-purified material as a template. In some cases a second gel purification is done using the amplified material from the first gel purification.

Mixing of Components to Generate Allelic Ladder

Primary or secondary reactions from selected genomic DNA templates or isolated amplified alleles are mixed, diluted, and amplified to generate an allelic ladder. This product may be detected, for example, by silver stain or ethidium bromide detection.

A fluorescently labeled allelic ladder is generated following mixing and dilution, by amplification using one or more fluorescently labeled locus-specific primers in place of, or in combination with, the unlabeled locus-specific primers. Primers are, for example, of the sequences described in Table 1 and are fluorescently labeled, for example, at the 5' terminus of the primer with fluorescent moieties using methods known to those skilled in the art.

Use of Ladder to Evaluate Samples of Unknown Allelic Content

The allelic ladder is used, inter alia, to determine the allelic content at the particular locus for DNA samples being tested. Side-by-side comparison of an amplified sample with an allelic ladder allows rapid visual determination of allele sizes within the sample without the need for calculation or additional analysis. This precision allows allelic ladders to be used as standards for identifying alleles within the same gel, on different gels, and with work performed in different laboratories.

Overview of Short Tandem Repeat DNA Profiling

DNA Extraction Methods

Prior to amplification, a sample of DNA from an individual organism is obtained. All nucleated cells contain genomic DNA and are potential sources of the required DNA. Blood cells are typically used for higher animals. Hair, semen and other tissue can also be used. Additionally, placental cells or fetal cells present in amniotic fluid or chorionic villi samples can be used for fetal analysis.

DNA can be isolated from blood using standard methods. See, for instance, Higuchi (1989), Walsh et al. (1991), and Miller et al. (1988). DNA concentrations are measured fluorometrically, Brunk et al. (1979).

DNA extraction generally involves digesting cells with a protease that does not attack DNA at a temperature and pH that reduces the likelihood of DNase activity. DNA isolation techniques are well known to the art. Reference is made to Kan et al. (1974, 1977 and 1978), which are incorporated herein by reference for their description of DNA isolation techniques.

Two DNA isolation methods are preferred to prepare DNA for amplification. The first method utilizes "CHELEX 100"® solution as a medium for DNA extraction. See Walsh et al. (1991). A 5% "CHELEX 100"® solution (5 g of "CHELEX 100"® to 100 ml sterile, deionized water) is required. The DNA extraction process is as follows:

1. For each blood sample, pipet 1 ml of sterile, deionized H$_2$O into a sterile 1.5 ml microcentrifuge tube. Add one of the following:
   a. 3–300 µl whole blood
   b. 3–5 mm square portion of bloodstained material
2. Gently mix the samples and incubate at room temperature for 30 minutes. Mix occasionally by inversion or gentle vortexing.
3. Centrifuge the samples at room temperature in a microcentrifuge for 2 minutes at 15,000×g.
4. Carefully remove all but 20–30 µl of the supernatant from each sample and discard. If the sample is a bloodstain, leave the fabric in the tube with the pellet.
5. Add 5% "CHELEX 100"® to a final volume of 200 µl. Pipet the 5% "CHELEX 100"® from a beaker with a stir bar continuously stirring the solution.
6. Incubate the samples at 56° C. for 20 minutes.
7. Vortex the samples on high speed for 5–10 seconds.
8. Incubate the samples at 100° C. for 8 minutes.
9. Vortex the samples on high speed for 5–10 seconds.
10. Centrifuge the samples at room temperature in a microcentrifuge for 2 minutes at 15,000×g.
11. The samples are now ready for DNA amplification. 5 µl of the supernatant should be used in a 50 µl PCR reaction volume.
12. Store the remainder of the sample at 2–8° C. or frozen. Before using stored samples, repeat Steps 10–12.

The second method is entitled the Cell Lysis/Proteinase K DNA Extraction method, Higuchi (1989). The procedure is as follows:
1. For each blood sample, pipet 0.5 ml of lysis buffer (0.32 M sucrose, 10 mM Tris-HCl, pH 7.5, 5 mM MgCl$_2$, 1% "TRITON X-100" detergent) into a sterile 1.5 ml microcentrifuge tube. Add one of the following:
   a. 3–300 µl whole blood
   b. 3–5 mm square portion of bloodstained material
2. Centrifuge the samples at room temperature in a microcentrifuge for 20 seconds at 15,000×g.
3. Carefully remove and discard the supernatant from each sample.
4. Add 1.0 ml lysis buffer to resuspend each pellet. Vortex for 30 seconds.
5. Repeat Steps 2–4 two more times.
6. Centrifuge the samples at room temperature in a microcentrifuge for 20 seconds at 15,000×g.
7. Carefully remove and discard the supernatant from each sample.
8. Add 0.5 ml digestion buffer (10 mM Tris-HCl, pH 8.3, 50 mM KCl, 2.5 mM MgCl$_2$, 0.1 mg/ml gelatin (Sigma Cat. #G2500), 0.45% "NONIDET P40" (Sigma Cat. #N6507), 0.45% "TWEEN 20" detergent) and 3 µl Proteinase K (50 mg proteinase K added to 5 ml sterile deionized water) (10 mg/ml) to each sample.
9. Incubate the samples at 60° C. for 1 hour.
10. Incubate the samples at 95° C. for 10 minutes to inactivate the proteinase K.
11. Briefly centrifuge to bring the contents to the bottom of the tube, and store the samples at −20° C. 5 µl of the supernatant in a 50 µl PCR reaction volume is recommended.

Both of the above described methods are quick, easy and capable of extracting DNA from bloodstains and from as little as 3 µl of whole blood. Traditional DNA extraction methods such as phenol:chloroform extraction methods, Sambrook et al. (1989), or inorganic methods, Grimberg et al. (1989) and Miller et al. (1988), can also be used for STR analysis.

Amplification of DNA

Preferred amplification procedures are conducted as described above and in the Examples with respect to PCR amplification.

Polyacrylamide Gel Preparation and Polyacrylamide Gel Electrophoresis

Preferred gel preparation and electrophoresis procedures are conducted as described in Example 1.

Detection of Allelic Ladders

Allelic ladders may be detected using any of a number of reporter systems including staining, e.g., silver staining, radioisotopes, fluorescers, chemiluminescers and enzymes in combination with detectable substrates.

Traditional methods of DNA sequencing utilize a radio-labeled oligonucleotide primer or the direct incorporation of a radiolabeled nucleotide. Fluorescent labeled oligonucleotide primers can be used in place of radiolabeled primers for sensitive detection of DNA fragments (U.S. Pat. No. 4,855,225 to Smith et al.). Both methods may also be employed to detect the amplification products from STR loci.

Silver staining is also generally well-known to the art. Somerville and Wang (1981) and Boulikas and Hancock (1981) first described the detection of nucleic acids using a silver staining process. Bassam et al. (1991) describe a silver staining protocol for polymerase chain reaction (PCR) amplified DNA fragments.

Kits

The present invention is also directed to kits that contain the above-described allelic ladders and locus-specific primers. An illustrative kit includes a container having a locus-specific primer pair or separate containers containing each primer of a primer pair, an allelic ladder directed to the specific locus, and instructions for use of the kit. Other ingredients may also be included in the kit. For instance, the following items may be included, either inclusively or alternatively, in the kit: a sufficient quantity of enzyme for PCR amplification, amplification buffer to facilitate amplification, loading solution for preparation of the amplified material for gel electrophoresis, human genomic DNA as a control, size markers to insure that materials migrate as anticipated in the gel, and a protocol and manual to educate the user and to limit error in use.

The amounts of the various reagents in the kits can be varied depending on a number of factors, such as the optimum sensitivity of the process and the number of analyses to be run by the user. The instructions for use are suitable to enable an analyst to carry out the desired test. It is within the scope of this invention to provide manual test kits or test kits for use in automated analyzers.

EXAMPLES

The following Examples are included solely to aid in a complete understanding of the present invention and to assist one of ordinary skill in making and using the same. The Examples do not limit the scope of the invention described and claimed herein in any fashion.

Throughout the Examples, the designation "FL" preceeding the various Sequence Identification Numbers indicates that the specific primer is labeled with fluorescein at its 5' terminus. The designation "TMR" in front of the Sequence Identification Number indicates that the primer is labeled with tetramethylrhodamine at its 5' terminus. If no designation is indicated, the 5' terminus contains a hydroxyl (OH) group.

Example 1

Construction of Allelic Ladder for STR Locus D16S539

D16S539 is an STR locus on chromosome 16. For allelic ladder construction, approximately 155 human DNA samples were subjected to the PCR. (Note that multiple DNA samples can be screened simultaneously for the ladders by using multiple primers in a single reaction tube). Reactions were conducted in a 25 µl volume using 1x STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP), using 5 to 25 ng of template and 0.08 U Taq DNA Polymerase/µl.

Amplification primers were used in combination during the screening process and include: 0.8 µM each of D16S539 primers 1 (SEQ. ID. NO: 1) and 2 (FL-SEQ. ID. NO: 2), 0.6 µM each of D7S820 primers 1 (SEQ ID. NO: 3) and 2 (FL-SEQ. ID. NO: 4), 0.5 µM each of D13S317 primers 1 (SEQ ID. NO: 5) and 2 (FL-SEQ. ID. NO: 6), and 1.0 µM each of D5S818 primers 1 (SEQ ID. NO: 7) and 2 (FL-SEQ. ID. NO: 8).

A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

Amplification products were subjected to PAGE using a 4% gel in 0.5X TBE. The 32 cm gel was subjected to electrophoresis at 40 watts for at least 30 minutes prior to sample loading. The gel surface temperature was approximately 50° C. Two and a half microliters of product was mixed with 2.5 µl of loading solution (10 mM NaOH, 95% Formamide and 0.05% Bromophenol Blue), heated to 95° C. for 2 minutes, and quickly chilled on ice. Three microliters of the mixture was loaded onto the gels. Electrophoresis was allowed to proceed for forty-five to sixty minutes at pre-loading conditions. Products were visualized using either the "FLUORIMAGER" fluorescent scanner (Molecular Dynamics, Sunnyvale, Calif.) or the "FMBIO" fluorescent scanner (Hitachi Software Engineering, San Bruno, Calif.).

After the screening was completed, individual DNA samples were chosen for the ladder construction, preferably homozygotes for the specific alleles when possible. Primary reactions from 7 individual DNA samples were amplified in 100 µl reaction volumes using 1x STR Buffer, 50 to 250 ng of template, 0.01 U Taq DNA Polymerase/µl and 0.5 µM each of D16S539 primers 1 (SEQ. ID. NO: 1) and 2 (SEQ. ID. NO: 2). A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

Secondary amplifications were performed according to the following procedure: One microliter of a 1/200 dilution (1 µl into 199 µl water) of the primary amplification was amplified in a 500 µl volume. Reaction conditions were the same as for the primary reactions.

The secondary reactions were used to purify the ladder alleles from a denaturing PAGE gel as described in Table 2:

The isolated alleles were diluted by placing 1 µl of isolated allele into 199 µl water and 1 µl of the dilution was amplified in a 500 µl volume using 1x STR Buffer, 0.02 U Taq DNA Polymerase/µl and 2 µM each of D16S539 primers 1 (SEQ. ID. NO: 1) and 2 (SEQ. ID. NO: 2).

A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

The amplification products were then run on a 0.4% denaturing polyacrylamide gel and detected by silver staining.

TABLE 2

| Step | |
|---|---|
| 1 | 24 µl of sample was mixed with 12 µl of STR 2X loading solution |
| 2 | Samples denatured 5 minutes at 95° C. then chilled 2 to 5 minutes on ice before loading |
| 3 | 30 µl loaded onto a 6% denaturing polyacrylamide gel |
| 4 | Gel run, 1–3 hours |
| 5 | Gel stained in 0.5 µg/ml ethidium bromide, 15–30 minutes |
| 6 | Gel destained in water, 10–20 minutes |
| 7 | Gel visualized on transilluminator |
| 8 | Fragments excised from gel using razor blade |
| 9 | Gel fragment soaked in 100–400 µl TE(10 mM tris, pH 7.5, 1 mM EDTA) at 37° C., 4 hours to overnight |
| 10 | Gel fragment/TE transferred to a "ULTRAFREE" ®-MC (Millipore) 0.45 µm filter unit and microfuged for 5 minutes |
| 11 | Filtrate saved for reamplification |

Using the above protocol, alleles 5, 8, 9, 10, 11, 12, 13 and 14 of locus D16S539 were isolated. FIG. 1A is a photograph of an electrophoresis gel containing the individual D16S539 alleles. From left to right, FIG. 1A shows alleles 5, 8, 9, 10, 11, 12, 13 and 14 of locus D16S539. The lane numbers correspond to the number of repeats in each allele.

To produce a fluorescein-labeled allelic ladder, the gel-purified alleles were then mixed by adding various amounts of the individual alleles. This mixture was then diluted by placing 1 µl of the allelic mixture in 199 µl of distilled water. One microliter of this mixture was amplified in a 500 µl volume using 1x STR Buffer, 0.04 U Taq DNA Polymerase/µl and 2.0 µM each D16S539 primers 1 (FL-SEQ. ID. NO: 1) and 2 (SEQ. ID. NO: 2). A Thermal Cycler 480 was employed with the following amplification protocol: 96° C. for 2 min., then 10 cycles of 94° C. for 1 min., 64° C. for 1 min., and 70° C. for 1.5 min., followed by 40 cycles of 90° C. for 1 min., 64° C. for 1 min., 70° C. for 1.5 min, followed by 1 cycle of 60° C. for 30 minutes.

Amplified products were separated by denaturing PAGE on a 32 cm gel for 50 min. at 40 W and products were visualized by detection of the fluorescent signals using the "FLUORIMAGER" fluorescent scanner.

Figure 1B:
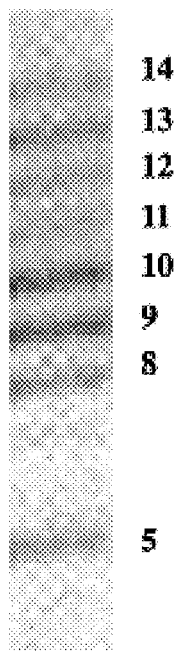
FIG. 1B is an image showing a fluorescent detection of the D16S539 allelic ladder according to the present invention. (See Example 1.)

FIG. 1B shows an electrophoresis gel of a D16S539 allelic adder containing alleles 5, 8, 9, 10, 11, 12, 13 and 14 according to the invention.

Example 2

Construction of Allelic Ladder for STR Locus D7S820

D7S820 is an STR locus on chromosome 7. A screening of approximately 155 human DNA samples was done simultaneously with the D16S539 locus as described in Example 1.

After the screening was complete, individual DNA samples were chosen for the ladder construction, preferably homozygotes for the specific alleles when possible. Primary reactions from 9 individual DNA samples were amplified in 300 µl reaction volumes using 1x STR Buffer, 50 to 250 ng of template, 0.03 U Taq DNA Polymerase/µl and 5.0 µM each of D7S820 primers 1 (SEQ. ID. NO: 9) and 2 (SEQ. ID. NO: 10).

A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

The primary reactions were used to purify the ladder alleles from a denaturing polyacrylamide gel. The gel purification procedure is described in Example 1, Table 2.

The isolated alleles were then diluted by placing 1 µl of isolated allele into 199 µl water and 1 µl of the dilution was amplified in a 500 µl volume using 1x STR Buffer, 0.02 U Taq DNA Polymerase/µl and 0.75 µM each of D7S820 primers 1 (SEQ. ID. NO: 9) and 2 (SEQ. ID. NO: 11).

A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

The amplification products were then run on a 0.4% denaturing PAGE gel and detected by silver staining.

Figure 2A:
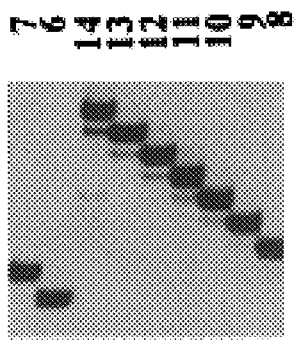
FIG. 2A is a photograph illustrating a silver stain detection of the individual alleles used in the construction of the D7S820 allelic ladder described in Example 2. The lanes labeled 6, 7, 8, 9, 10, 11, 12, 13, and 14 indicate the repeat number of each allele.

FIG. 2A is a photograph of an electrophoresis gel containing the individual alleles 6, 7, 8, 9, 10, 11, 12, 13 and 14 of the D7S820 locus. From left to right, FIG. 2A shows D7S820 repeats 6, 7, 8, 9, 10, 11, 12, 13 and 14. The lane numbers correspond to the number of repeats in each allele.

To produce a fluorescein-labeled ladder the gel-purified alleles were then mixed by adding various amounts of the individual alleles. This mixture was then diluted by placing 1 µl of the allelic mixture and placing in 199 µl of distilled water. One microliter of this mixture was amplified in a 300 µl volume using 1x STR Buffer, and 0.066 U Taq DNA Polymerase/µl and 2.0 µM each of D7S820 primers 1 (SEQ. ID. NO: 9) and 2 (FL-SEQ. ID. NO: 11).

A Thermal Cycler 480 was employed with the following amplification protocol: 96° C. for 2 min., then 10 cycles of 94° C. for 1 min., 60° C. for 1 min., and 70° C. for 1.5 min., followed by 30 cycles of 90° C. for 1 min., 60° C. for 1 min., 70° C. for 1.5 min. followed by 1 cycle of 60° C. for 30 minutes.

Figure 2B:
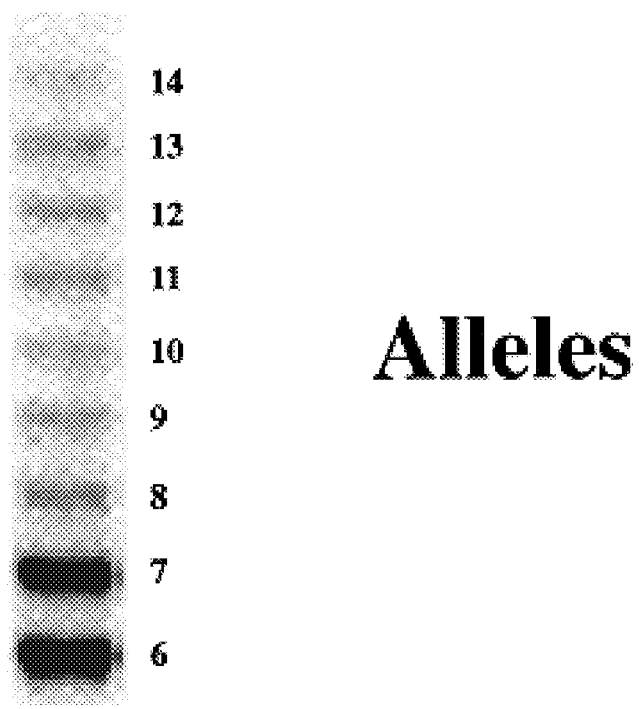
FIG. 2B is an image showing a fluorescent detection of the D7S820 allelic ladder according to the present invention. (See Example 2.)

Amplified products were separated by denaturing PAGE on a 32 cm gel for 50 min. at 40 W and products were visualized by detection of the fluorescent signals using the "FMBIO" Fluorescent Scanner. FIG. 2B is a photograph of the resultant gel of the D7S820 allelic ladder. The ladder containing alleles 6, 7, 8, 9, 10, 11, 12, 13 and 14 of the D7S820 locus.

Example 3

Construction of Allelic Ladder for STR Locus D13S317

D13S317 is an STR locus on chromosome 13. A screening of approximately 155 human DNA samples was done simultaneously with the D16S539 locus as described in Example 1.

After the screening was complete, individual DNA samples were chosen for the ladder construction, preferably homozygotes for the specific alleles when possible. Primary reactions from 7 individual DNA samples were amplified in 300 µl reaction volumes using 1x STR Buffer, 50 to 250 ng of template, 0.03 U Taq DNA Polymerase/µl and 5.0 µM each of D13S317 primers 1 (SEQ. ID. NO: 5) and 2 (SEQ. ID. NO: 6).

A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

The primary reactions were used to purify the ladder alleles from a denaturing PAGE gel. The gel purification procedure is described in Example 1, Table 2.

The isolated alleles were then diluted by placing 1 µl of isolated allele into 199 µl water and 1 µl of the dilution was amplified in a 500 µl volume using 1x STR Buffer, 0.02 U Taq DNA Polymerase/µl and 2.0 µM each of D13S317 primers 1 (SEQ. ID. NO: 5) and 2 (SEQ. ID. NO: 6).

A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

Figure 3A:
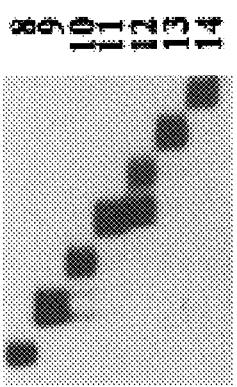
FIG. 3A is a photograph illustrating a silver stain detection of the individual alleles used in the construction of the D13S317 ladder described in Example 3. The lanes labeled 8, 9, 10, 11, 12, 13, and 14 indicate the repeat number of each allele.

The amplifications were then run on a 0.4% denaturing PAGE gel and detected by silver staining. FIG. 3A is a photograph of an electrophoresis gel containing isolated alleles 8, 9, 10, 11, 12, 13 and 14 of locus D13S317 yielded using this protocol. From left to right, individual alleles 8, 9, 10, 11, 12, 13 and 14 of D13S317 are shown in FIG. 3A. The lane numbers correspond to the number of repeats in each allele.

To produce a fluorescein-labeled ladder the gel-purified alleles were then mixed by adding various amounts of the individual alleles. This mixture was then diluted by placing 1 µl of the allelic mixture and placing in 199 µl of distilled water. One microliter of this mixture was amplified in a 300 µl volume using 1x STR Buffer, and 0.066 U Taq DNA Polymerase/µl and 2.0 µM each of D13S317 primers 1 (SEQ. ID. NO: 5) and 2 (FL-SEQ. ID. NO: 6).

A Thermal Cycler 480 was employed with the following amplification protocol: 96° C. for 2 min., then 10 cycles of 94° C. for 1 min., 58° C. for 1 min., and 70° C. for 1.5 min., followed by 30 cycles of 90° C. for 1 min., 58° C. for 1 min., 70° C. for 1.5 min. followed by 1 cycle of 60° C. for 30 minutes.

Figure 3B:
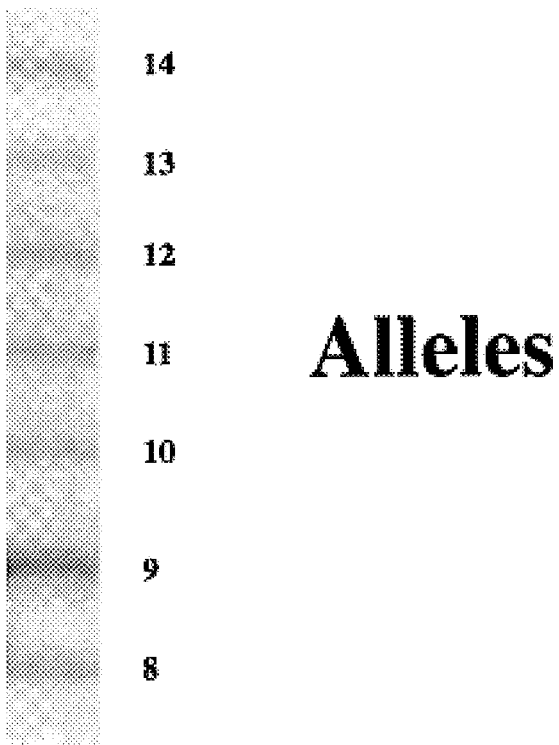
FIG. 3B is an image showing a fluorescent detection of the D13S317 allelic ladder according to the present invention. (See Example 3.)

Amplified products were separated by denaturing PAGE on a 32 cm gel for 50 min. at 40 W and products were visualized by detection of the fluorescent signals using the "FLUORIMAGER" fluorescent scanner. FIG. 3B shows an electrophoresis gel of the D13S317 allelic ladder containing alleles 8, 9, 10, 11, 12, 13 and 14.

Example 4

Construction of Allelic Ladder for STR Locus D5S818

D5S818 is an STR locus on chromosome 5. A screening of approximately 155 human DNA samples was done simultaneously with the D16S539 locus as described in Example 1.

After the screening was complete, individual DNA samples were chosen for the ladder construction, preferably homozygotes for the specific alleles when possible. Primary reactions from 8 individual DNA samples were amplified in 300 µl reaction volumes using 1x STR Buffer, 50 to 250 ng of template, 0.02 U Taq DNA Polymerase/μl and 5.0 μM each of D5S818 primers 1 (SEQ. ID. NO: 12) and 2 (SEQ. ID. NO: 13).

A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

The primary reactions were used to purify the ladder alleles from a denaturing PAGE gel. The gel purification procedure is described in Example 1, Table 2.

The isolated alleles were then diluted by placing 1 μl of isolated allele into 199 μl water and 1 μl of the dilution was amplified in a 500 μl volume using 1x STR Buffer, 0.02 U Taq DNA Polymerase/μl and 2.0 μM each of D5S818 primers 1 (SEQ. ID. NO: 12) and 2 (SEQ. ID. NO: 13).

A Thermal Cycler 480 was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 minutes.

The amplifications were then run on a 0.4% denaturing PAGE gel and detected by silver staining.

Figure 4A:
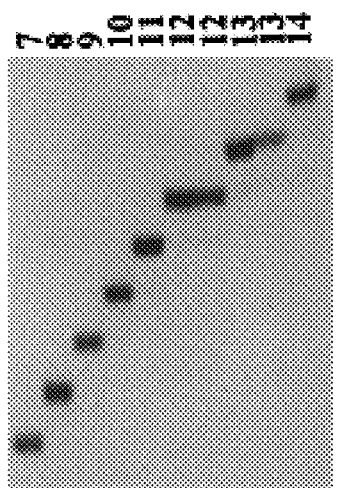
FIG. 4A is a photograph illustrating a silver stain detection of the individual alleles used in the construction of the D5S818 ladder described in Example 4. The lanes labeled 7, 8, 9, 10, 11, 12, 13, and 14 indicate the repeat number of each allele.

Reference is now made to FIG. 4A, which is a photograph illustrating the individual D5S818 alleles containing repeats 7, 8, 9, 10, 11, 12, 13 and 14. The lane numbers in FIG. 4A correspond to the number of repeats in each allele.

To produce a fluorescein-labeled ladder, the gel-purified alleles were then mixed by adding various amounts of the individual alleles. This mixture was then diluted by placing 1 μl of the allelic mixture and placing in 199 μl of distilled water. One microliter of this mixture was amplified in a 300 μl volume using 1x STR Buffer, and 0.066 U Taq DNA Polymerase/μl and 2.0 μM each of D5S818 primers 1 (SEQ. ID. NO: 12) and 2 (FL-SEQ. ID. NO: 13).

A Thermal Cycler 480 was employed with the following amplification protocol: 96° C. for 2 min., then 10 cycles of 94° C. for 1 min., 60° C. for 1 min., and 70° C. for 1.5 min., followed by 30 cycles of 90° C. for 1 min., 60° C. for 1 min., 70° C. for 1.5 min, followed by 1 cycle of 60° C. for 30 minutes.

Figure 4B:
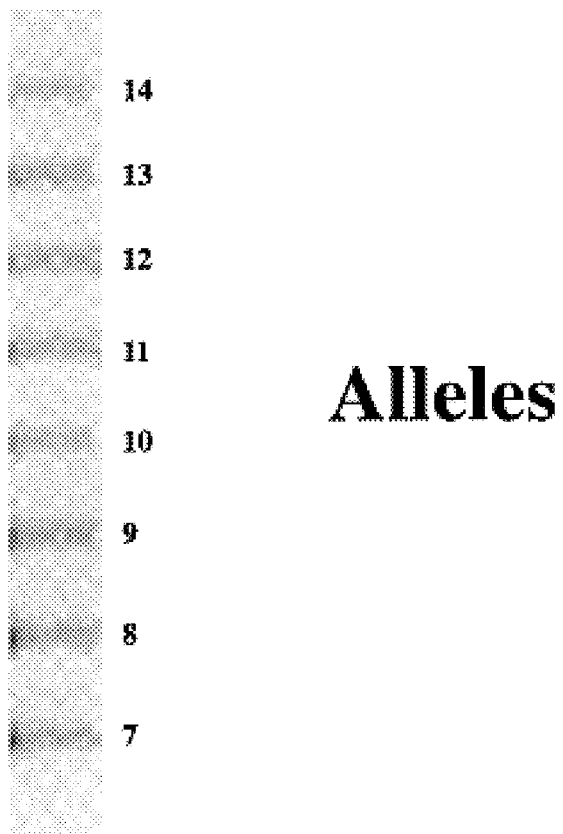
FIG. 4B is an image showing a fluorescent detection of the D5S818 allelic ladder according to the present invention. (See Example 4.)

Amplified products were separated by denaturing PAGE on a 32 cm gel for 50 min. at 40 W and products were visualized by detection of the fluorescent signals using the "FLUORIMAGER" fluorescent scanner. FIG. 4B shows an electrophoresis gel of the D5S818 allelic ladder containing alleles 7, 8, 9, 10, 11, 12, 13 and 14.

Example 5

Application of Allelic Ladders to Obtain High Throughput Analysis of Multiple Loci for Typing of Individuals Genomic DNA samples were amplified in one reaction at the D16S539, D7S820, D13S317 and D5S818 loci. The corresponding allelic ladders were mixed in one tube and loaded into a single PAGE lane. Gel electrophoresis and detection using the "FMBIO" fluorescent scanner were performed as described in Example 1.

Figure 5:
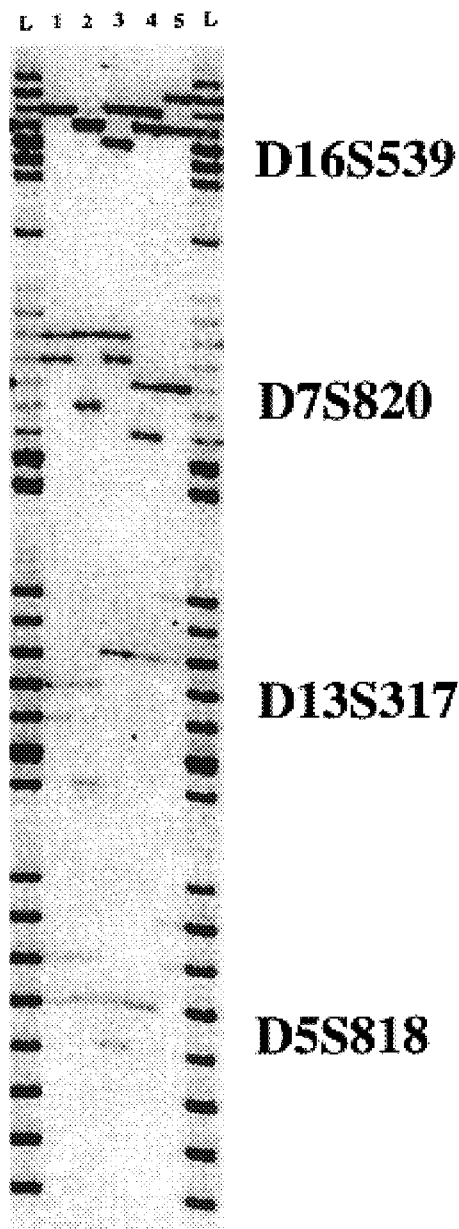
FIG. 5 is an image showing four allelic ladders for the loci D16S539, D7S820, D13S317 and D5S818 which have been mixed and loaded (in duplicate) into the lanes marked L. Lanes 1 through 5 are DNA samples which were simultaneously amplified for all four loci in one tube.

Reference is now made to FIG. 5 which illustrates independent analysis of each amplified region by comparison with the corresponding allelic ladder in a single gel lane. Lanes labeled L contain the allelic ladder mixture and lanes 1–5 contain human DNA samples that have been amplified in a multiplex reaction. The samples would be typed as shown in Table 3.

TABLE 3

| Locus | Lane Number | Alleles Present |
|---|---|---|
| D16S539 | 1 | 12,12 |
|  | 2 | 11,11 |
|  | 3 | 12,10 |
|  | 4 | 12,11 |
|  | 5 | 13,11 |
| D7S820 | 1 | 12,11 |
|  | 2 | 12,9 |
|  | 3 | 12,11 |
|  | 4 | 10,8 |
|  | 5 | 10,10 |
| D13S317 | 1 | 11,10 |
|  | 2 | 11,8 |
|  | 3 | 12,12 |
|  | 4 | 12,12 |
|  | 5 | 14,12 |
| D5S818 | 1 | 12,11 |
|  | 2 | 12,11 |
|  | 3 | 11,10 |
|  | 4 | 11,11 |
|  | 5 | 13,12 |

It is understood that the present invention is not limited to the embodiments described hereinabove, but includes all modifications and equivalents thereof as come within the scope of the attached claims.

BIBLIOGRAPHIC CITATION

Patents

U.S. Pat. No. 4,855,225 to Smith et al.
U.S. Pat. No. 5,192,659 to Simons.

Publications

Bassam et al. (1991) *Anal. Biochem.* 196:80–83.
Beckmann and Weber (1992) *Genomics* 12:627–631.
Botstein et al. (1980) *Am. J. Hum. Genet.* 32:314–331.
Boulikas and Hancock (1981) *J. Biochem. Biophy. Meth.* 5:219–228.
Brinkmann (1992) *Proceedings from the Third International Symposium on Human Identification* (Promega, Madison, Wis.) pp. 357–373.
Brunk et al. (1979) *Anal Biochem* 92:497–500.
Budowle et al. (1991) *Am J Hum Genet* 48:137–144.
Edwards et al. (1991a) *Proceedings from the Second International Symposium on Human Identification* (Promega Corporation) p. 31–52.
Edwards et al. (1991b) *Am J Hum Genet* 49:746–756.
Edwards (1992) *Genomics* 12:241–253.
Frank and Koster (1979) *Nucleic Acids Res.* 6:2069–2087.
Gill et al. (1985) *Nature* 318:577–579.
Grimberg et al. (1989) *Nucl. Acids Res.* 17:8390.
Higuchi (1989) *Amplifications: A Forum for PCR Users* (May 1989), Perkin Elmer Cetus, Norwalk, Conn., Issue 2.
Jeffreys et al. (1985) *Nature* 316:76–79.
Jones (1972) *J. Forensic Sci. Soc.* 12:355–359.
Kan et al. (1974) *Nature,* 251:392.
Kan et al. (1977) *N. Engl. J. Med.,* 297:1080–1084.
Kan et al. (1978) *PNAS,* 75:5631–5635.
Litt and Luty (1989) *Am J Hum Genet* 44:397–401.
Martin et al. (1991) *BioTechniques* 11:110–113.
Maxam and Gilbert (1977) *Proc. Natl. Acad. Sci. USA* 74:560.

Maxam and Gilbert (1980) *Meth. Enzymol.* 65:499.
Miller et al. (1988) *Nucl. Acids Res.* 16:1215.
Nakamura et al. (1987) *Science* 235:1616–1622.
Patel et al. (1984) *Somat Cell Mol Genet* 10:483–493.
Puers et al. (1993) *Am. J. Hum. Genet.,* 53:953–958.
Sambrook et al. (eds) (1989) *Molecular Cloning-A Laboratory Manual,* 2nd edition, Cold Spring Harbor Laboratory Press.
Sanger et al. (1977) *Proc. Natl. Acad. Sci. USA* 74:5463–5467.
Smith (1995) Biotechniques 18:122–128.
Somerville and Wang (1981) *Biochem. Biophys. Res. Comm.* 102: 53–58.
Sprecher et al. (1996) *BioTechniques* 20:266–276.
Tautz (1989) *Nucleic Acids Res.* 17:6463–6471.
Voss et al. (1992) *Meth. Mol. Cell Biol.,* 3:30–34.
Walsh et al. (1991) *BioTechniques* 10:506–513.
Watson, J. D. et al. (1987) *Mol. Biol. Gene*, The Benjamin/Cummings Publishing Company, Inc., California, pp. 274–276.
Weber and May (1989) *Am J Hum Genet* 44:388–396.

What is claimed is:

1. An allelic ladder of a short tandem repeat locus comprising, in combination, an isolated plurality of DNA molecules which are allelic variants of a polymorphic short tandem repeat locus, each DNA molecule comprising a polymorphic tandemly repeated base pair motif and non-polymorphic 5' and 3' flanking regions, wherein the polymorphic short tandem repeat locus is selected from the group consisting of D16S539, D7S820, D13S317, and D5S818.

2. The allelic ladder of claim 1, wherein the short tandem repeat locus is D16S539.

3. The allelic ladder of claim 1, wherein the short tandem repeat locus is D7S820.

4. The allelic ladder of claim 1, wherein the short tandem repeat locus is D13S317.

5. The allelic ladder of claim 1, wherein the short tandem repeat locus is D5S818.

6. A kit for analyzing short tandem repeat sequences from a DNA sample, the kit comprising at least one receptacle containing one or more allelic ladders as recited in claim 1.

7. The kit of claim 6, wherein the allelic ladder is of the short tandem repeat locus D16S539.

8. The kit of claim 6, wherein the allelic ladder is of the short tandem repeat locus D7S820.

9. The kit of claim 6, wherein the allelic ladder is of the short tandem repeat locus D13S317.

10. The kit of claim 6, wherein the allelic ladder is of the short tandem repeat locus D5S818.

11. The kit of claim 6, further comprising at least one other receptacle containing one or more corresponding oligonucleotide primers or primer pairs which specifically prime PCR amplification of the DNA molecules.

12. The kit of claim 6, further comprising instructions for use of the kit.

13. A method for detecting and identifying alleles of a short tandem repeat sequence from DNA comprising:

(a) amplifying at least one short tandem repeat sequence from a target DNA by polymerase chain reaction using locus-specific oligonucleotide primers, wherein the at least one short tandem repeat sequence is located within at least one short tandem repeat locus selected from the group consisting of D16S539, D7S820, D13S317, D5S818, and combinations thereof; and then (b) comparing the at least one amplified short tandem repeat sequence to an allelic ladder as recited in claim 1 corresponding to the at least one short tandem repeat locus.

14. The method of claim 13, wherein in step (a) the at least one short tandem repeat sequence is amplified from a target DNA by polymerase chain reaction using locus-specific oligonucleotide primers selected from the group consisting of SEQ. ID. NOS: 1–12 and 13.

15. The method of claim 13, wherein in step (b), the at least one amplified short tandem repeat sequence is compared to the corresponding allelic ladder by gel electrophoresing the amplified short tandem repeat sequence and the allelic ladder in separate or the same lanes of an electrophoretic gel and comparing banding patterns of the allelic ladder and the amplified sample.

16. A method for simultaneously detecting and identifying alleles of four short tandem repeat sequences from DNA comprising:

(a) co-amplifying four short tandem repeat sequences from a target DNA by polymerase chain reaction using locus-specific oligonucleotide primers for the four short tandem repeat sequences, wherein the four short tandem repeat sequences are located within four short tandem repeat loci selected from the group consisting of D16S539, D7S820, D13S317, and D5S818; and then (b) comparing the four co-amplified short tandem repeat sequences to an allelic ladder as recited in claim 1 corresponding to each of the four short tandem repeat loci.

17. The method according to claim 16, wherein in step (b), the four co-amplified short tandem repeat sequences and the corresponding allelic ladder are compared by gel electrophoresis in parallel lanes, and further wherein alleles of the four co-amplified short tandem repeat sequences do not physically overlap in gel electrophoresis.

18. A kit for analyzing a short tandem repeat sequence from a DNA sample, the kit comprising at least one receptacle containing an isolated plurality of DNA molecules which are allelic variants of a polymorphic short tandem repeat locus, each DNA molecule comprising a polymorphic tandemly repeated base pair motif and non-polymorphic 5' and 3' flanking regions, wherein the polymorphic short tandem repeat locus is selected from the group consisting of D16S539, D7S820, D13S317, and D5S818.

19. The kit of claim 18, further comprising an oligonucleotide primer pair which hybridize solely with alleles of the polymorphic short tandem repeat locus.

20. The kit of claim 19, wherein at least one primer of each oligonucleotide primer pair is selected from the group consisting of:

SEQ ID NO: 1 and SEQ ID NO:2 when the short tandem repeat locus is D16S539;

SEQ ID NO:3 and SEQ ID NO:4 when the short tandem repeat locus is D7S820;

SEQ ID NO:5 and SEQ ID NO:6 when the short tandem repeat locus is D13S317; and

SEQ ID NO:7 and SEQ ID NO:8 when the short tandem repeat locus is D5S818.

* * * * *

UNITED STATES PATENT AND TRADEMARK OFFICE
CERTIFICATE OF CORRECTION

PATENT NO. : 6,156,512
DATED : December 5, 2000
INVENTOR(S) : Schumm et al.

It is certified that error appears in the above-identified patent and that said Letters Patent is hereby corrected as shown below:

<u>Title Page,</u>
Item [73] insert:

Assignee:     Promega Corporation
                      Madison, Wisconsin

Signed and Sealed this

Twenty-fifth Day of September, 2001

*Attest:*

*Nicholas P. Godici*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GGGGGTCTAA GAGCTTGTAA AAAG                                    24

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TGTGCATCTG TAAGCATGTA TCTATC                                 26

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

GAACACTTGT CATAGTTTAG AACG                                    24

(2) INFORMATION FOR SEQ ID NO:4:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

CTGAGGTATC AAAAACTCAG AGG                                          23

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACAGAAGTCT GGGATGTGGA                                              20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCCCAAAAAG ACAGACAGAA                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGGTGATTTT CCTCTTTGGT                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TGATTCCAAT CATAGCCACA                                              20

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATGTTGGTCA GGCTGACTAT G                                            21

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CCACATTTAT CCTCATTGAC AG                                      22
```

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
TCCACATTTA TCCTCATTGA CAG                                     23
```

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GGGTGATTTT CCTCTTTGGT ATCC                                    24
```

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
AGTGATTCCA ATCATAGCCA CAG                                     23
```

(2) INFORMATION FOR SEQ ID NO:14:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
ATGGCTGCCC TCACGGCTGC ACCGGGAGGA TGACTGTNTT                    40
CCCACTCTCA GTCCTGCCGA GGTGCCTGAC AGCCCTGCAC                    80
CCAGGAGCTG GGGGGTCTAA GAGCTTGTAA AAAGTGTACA                   120
AGTGCCAGAT GCTCGTTGTG CACAAATCTA AATGCAGAAA                   160
```

```
AGCACTGAAA GAAGAATCCA GAAAACCACA GTTCCCATTT              200

TTATATGGGA GCAAACAAAG GCAGATCCCA AGCTCTTCCT              240

CTTCCCTAGA TCAATACAGA CAGACAGACA GGTGGATAGA              280

TAGATAGATA GATAGATAGA TAGATAGATA GATAGATATC              320

ATTGAAAGAC AAAACAGAGA TGGATGATAG ATACATGCTT              360

ACAGATGCAC ACACAAACGT AAATGGTATN AAAAATNGGA              400

TNCACTCTTG TANGGTTGTT NTTACC                             426

(2) INFORMATION FOR SEQ ID NO:15:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AATTTTTGTA TTTTTTTTAG AGACGGGGTT TCACCATGTT              40

GGTCAGGCTG ACTATGGAGT TATTTTAAGG TTAATATATA              80

TAAAGGGTAT GATAGAACAC TTGTCATAGT TTAGAACGAA              120

CTAACGATAG ATAGATAGAT AGATAGATAG ATAGATAGAT              160

AGATAGATAG ATAGACAGAT TGATAGTTTT TTTTTATCTC              200

ACTAAATAGT CTATAGTAAA CATTTAATTA CCAATATTTG              240

GTGCAATTCT GTCAATGAGG ATAAATGTGG AATCGTTATA              280

ATTCTTAAGA ATATATATTC CCTCTGAGTT TTTGATACCT              320

CAGATTTTAA GGCC                                          334

(2) INFORMATION FOR SEQ ID NO:16:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TGGGATGGGT TGCTGGACAT GGTATCACAG AAGTCTGGGA              40

TGTGGAGGAG AGTTCATTTC TTTAGTGGGC ATCCGTGACT              80

CTCTGGACTC TGACCCATCT AACGCCTATC TGTATTTACA              120

AATACATTAT CTATCTATCT ATCTATCTAT CTATCTATCT              160

ATCTATCTAT CTATCTATCA ATCATCTATC TATCTTTCTG              200

TCTGTCTTTT TGGGCTGCCT ATGGCTCAAC CCAAGTTGAA              240

GGAGGAGATT TGACCAACAA TTCAAGCTCT CTGAATATGT              280

TTTGAA                                                   286

(2) INFORMATION FOR SEQ ID NO:17:

(i) SEQUENCE CHARACTERISTICS:
```

```
        (A) LENGTH: 307 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TCTAATTAAA GTGGTGTCCC AGATAATCTG TACTAATAAA                              40

AGTATATTTT AATAGCAAGT ATGTGACAAG GGTGATTTTC                              80

CTCTTTGGTA TCCTTATGTA ATATTTTGAA GATAGATAGA                             120

TAGATAGATA GATAGATAGA TAGATAGATA GATAGGTAGA                             160

TAGAGGTATA AATAAGGATA CAGATATAGN TACAAATGTT                             200

GTAAACTGTG GCTATGATTG GAATCACTTG GCTAAAAAGC                             240

GCTNAAGCNT TCCTCTGNGA GAGGCAATTA CTTTTTTNCT                             280

TAGGNACTNC CTCANCAGTC TNTTNGC                                           307
```